United States Patent [19]

Nguyen

[11] Patent Number: 5,386,000

[45] Date of Patent: * Jan. 31, 1995

[54] LOW TEMPERATURE FLEXIBLE DIE ATTACH ADHESIVE AND ARTICLES USING SAME

[75] Inventor: My N. Nguyen, San Diego, Calif.

[73] Assignee: Johnson Matthey Inc., Valley Forge, Pa.

[ * ] Notice: The portion of the term of this patent subsequent to Sep. 22, 2009 has been disclaimed.

[21] Appl. No.: 162,389

[22] Filed: Dec. 3, 1993

Related U.S. Application Data

[63]. Continuation of Ser. No. 843,738, Feb. 28, 1992, abandoned, and a continuation-in-part of Ser. No. 602,504, Oct. 24, 1990, Pat. No. 5,150,195.

[51] Int. Cl.$^6$ ............................................. C08G 63/44
[52] U.S. Cl. ................................... 528/362; 252/512; 252/514; 523/400; 523/416; 528/363; 528/422
[58] Field of Search ..................... 528/363, 422, 362; 523/400, 416; 252/512, 514

[56] References Cited

U.S. PATENT DOCUMENTS

| | | |
|---|---|---|
| 1,743,167 | 1/1930 | Styer . |
| 2,895,270 | 7/1959 | Blaess . |
| 3,586,926 | 6/1971 | Nakamura et al. . |
| 3,595,900 | 7/1971 | Loudas et al. . |
| 4,280,885 | 7/1981 | Savery . |
| 4,375,498 | 3/1983 | Le Minez et al. . |
| 4,401,776 | 8/1983 | Munk . |
| 4,552,690 | 11/1985 | Ikeguchi et al. ..................... 252/512 |
| 4,604,452 | 8/1986 | Shimp . |
| 4,608,434 | 8/1986 | Shimp . |
| 4,699,888 | 10/1987 | Dumesnil et al. . |
| 4,709,008 | 11/1987 | Shimp . |
| 4,732,702 | 3/1988 | Yamazaki et al. . |
| 4,740,584 | 4/1988 | Shimp . |
| 4,740,830 | 4/1988 | Ketley . |
| 4,785,075 | 11/1988 | Shimp . |
| 4,831,086 | 5/1989 | Das et al. . |
| 4,839,442 | 6/1989 | Craig, Jr. . |
| 4,847,233 | 7/1989 | Shimp . |
| 4,861,823 | 8/1989 | Qureshi . |
| 4,902,752 | 2/1990 | Shimp . |
| 4,931,545 | 6/1990 | Shimp et al. . |
| 4,940,848 | 7/1990 | Shimp . |
| 4,983,683 | 1/1991 | Shimp . |
| 4,999,699 | 3/1991 | Christie et al. . |
| 5,002,818 | 3/1991 | Licari et al. . |
| 5,037,691 | 8/1991 | Medney et al. . |
| 5,068,309 | 11/1991 | Shimp . |
| 5,114,003 | 5/1992 | Jackisch et al. . |
| 5,149,863 | 9/1992 | Shimp et al. . |
| 5,150,195 | 9/1992 | Nguyen ............................. 252/512 |
| 5,155,066 | 10/1992 | Nguyen . |
| 5,162,574 | 11/1992 | Craig, Jr. . |
| 5,195,299 | 3/1993 | Nguyen . |
| 5,250,600 | 10/1993 | Nguyen et al. ..................... 524/377 |

OTHER PUBLICATIONS

D. A. Shimp and W. M. Craig, Jr., "New Liquid Dicyanate Monomer for Rapid Impregnation of Reinforcing Fibers," 34th International SAMPE Symposium, 1989 (1).

Hi-Tek Polymers, "AroCy ® Cyanate Ester Safety and Handling Bulletin, AroCy ® Safety and Handling" (1).

Hans Steinegger, "Smart Cards: Bonding Technology at its Limits," Microeletronics Mfg. Tech., Dec. 1992, pp. 13-15 (2).

D. A. Shimp, et al., "AroCy ® Cyanate Ester Resin, Chemistry, Properties and Applications," Rhône-Poulenc, Inc.; Jan. 1990, pp. 1-36. (1).

E. Grigat and R. Putter, "New Methods of Preparative Organic Chemistry VI-Synthesis and Reactions of Cyanic Esters," Agnew. Chem. Internat. Edit., vol. 6, Nov. 3, 1967, pp. 206-216.

Hi-Tek Polymers, "AroCy ® L-10 Cyanate Ester Monomer," Oct. 1989. (1).

Hi-Tek Polymers, "AroCy ® Cyanate Ester Resins." (1).

Hi-Tek Polymers, "AroCy ® F-40S Cyanate Ester Resin Solution," Apr. 1989.

Hi-Tek Polymers, "AroCy ® B-10 Cyanate Ester Monomer," Oct. 1988.

Hi-Tek Polymers, "AroCy ® B-40S Cyanate Ester Resin Solution," Oct. 1988.

Hi-Tek Polymers, "AroCy ® B-50 Cyanate Ester Hard Resin," Oct. 1988.

Hi-Tek Polymers, "AroCy ® M-10 Cyanate Ester Monomer," Oct. 1988.

Hi-Tek Polymers, "AroCy ® M-30 Cyanate Ester Semisolid Resin," Oct. 1988.

Hi-Tek Polymers, "AroCy ® M-40S Cyanate Ester Resin Solution," Oct. 1988.

Hi-Tek Polymers, "AroCy ® M-50 Cyanate Ester Hard Resin," Oct. 1988.

Hi-Tek Polymers, "AroCy ® T-30 Cyanate Ester Semisolid Resin," Oct. 1988.

Allied Signal Inc., "Primaset—PT Resins, Safety and Handling Bulletin," Mar. 20, 1992.

(List continued on next page.)

Primary Examiner—John Kight, III
Assistant Examiner—John M. Cooney, Jr.
Attorney, Agent, or Firm—Christie, Parker & Hale

[57] ABSTRACT

Described is a flexible adhesive formulation for bonding a semiconductor device to a flexible substrate and a flexible card containing a semiconductor device which can be processed in a computer.

9 Claims, 3 Drawing Sheets

OTHER PUBLICATIONS

Allied Signal Inc., "Primaset—PT Resins".

Allied-Signal Inc., "Primaset—PT Resins, Literature List".

Tactix Performance Polymers, "XU-71787.02, XU-71787.07, Developmental Polycyanate Resins for Advanced Composites and Adhesives".

Sajal Das, "Phenol-Triazine (PT) Resin, A New Family of High Performance Thermosets" Cyanate Ester Symposium, Apr. 9-10, 1992.

D. A. Shimp and S. J. Ising, "Moisture Effects and their Control in the Curing of Polycyanate Resins," Cyanate Ester Symposium, Apr. 9-10, 1992. (1).

S. L. Simon and J. K. Gillham, "Cure of a Dicyanate Ester/Polycyanurate System," Cyanate Ester Symposium, Apr. 9-10, 1992 (1).

Fraunhofer Institut fur Angewandte Materialforschung, "Polycyanurates and Their Modifications, State of the Art and New Aspects," Gordon Research Conference on Thermoset, Jun. 1993. (1).

Hi-Tek Polymers, "AroCy® Resins," Dec. 1988. (1).

David Shimp and Mark Southcott, "Controlling Moisture Effects During the Curing of High $T_g$ Cyanate Ester/Aramid Composites," 38th International Symposium and Exhibition, May 10-13, 1993. (1).

Rhône-Poulenc, "Specialty Resins—Reactive Rubber Tougheners for AroCy® Cyanate Ester Resins," Jan. 1991.

Rhône-Poulenc, "Specialty Resins—Pyrolysis of AroCy® Cyanate Esters".

Rhône-Poulenc, "Specialty Resins—Quantative Determination of Residual Cyanate in Cured Homopolymers Via FTIR Analysis," Jan. 2, 1992.

Rhône-Poulenc, "Specialty Resins—Compatibility of Cyanate Esters with Aramid Reinforcements and Polyamide/Imide Substrates".

Rhône-Poulenc, "Specialty Resins—AroCy® L-10 Cyanate Ester Monomer," Sep. 1990. (1).

Rhône-Poulenc, "Specialty Resins—AroCy® F-10 Cyanate Ester Monomer," Sep. 1990.

Rhône-Poulenc, "Specialty Resins—AroCy® M-20 Low Melt Viscosity Prepolymer," Sep. 1990.

Rhône-Poulenc, "Specialty Resins—AroCy® B-10 Cyanate Ester Monomer," Oct. 1990.

Rhône-Poulenc, "Specialty Resins—Toxicity of AroCy® Cyanate Esters".

Rhône-Poulenc, "Specialty Resins—AroCy® M-10 Cyanate Ester Monomer," Sep. 1990.

Rhône-Poulenc, "Specialty Resins—AroCy® Cyanate Ester Resins".

Rhône-Poulenc, "Specialty Resins—AroCy® Cyanate Ester Resins" list.

Rhône-Poulenc, "Specialty Resins—AroCy® F-40S Cyanate Ester Resin Solution," Jul 1990.

Rhône-Poulenc, "Specialty Resins—AroCy® B-30 Cyanate Ester Semisolid Resin".

Rhône-Poulenc, "Specialty Resins—AroCy® B-40S Cyanate Ester Resin Solution," Aug. 1990.

Rhône-Poulenc, "Specialty Resins—AroCy® B-50 Cyanate Ester Hard Resin," Sep. 1990.

Rhône-Poulenc, "Specialty Resins—AroCy® M-40S Cyanate Ester Resin Solution," Aug. 1990.

Rhône-Poulenc, "Specialty Resins—AroCy® M-30 Cyanate Ester Semisolid Resin," Sep. 1990.

Rhône-Poulenc, "Specialty Resins—AroCy® M-50 Cyanate Ester Hard Resin," Sep. 1990.

Rhône-Poulenc, "Specialty Resins—AroCy® Cyanate Ester Safety and Handling Bulletin," Sep. 1990.

Rhône-Poulenc, "Specialty Resins—Formulating AroCy® Cyanate Esters for Resin Transfer Molding Applications," Apr. 1991.

Rhône-Poulenc, "Specialty Resins—AroCy® Cyanate Ester Adhesives for Polyimide Flexible Circuitry," Jan. 1991.(1).

Rhône-Poulenc, "Galvanic Corrosion of Carbon Fiber Composites," Jan. 1991.

Hi-Tek Polymers, "REX-378 Developmental Cyanate Ester Prepolymer."

Uri Sela and Hans Steinegger, "Dispensing Technology—The Key to High-Quality, High-Speed Die Bonding," *Microelectronics Manufacturing Technology*, Feb. 1991, pp. 47-52.

Jack R. Christenson and David A. Shimp, "Improvements in Performance and Processing Using Cyanate Ester Blends and Alloys," Ultralloy '90, pp. 191-208. (1).

Tony del Rosario, "JM 7000 Low Temperature Die Attach Material Qualification Report," Olin Interconnect Technologies, Dec. 10, 1992.

Malcolm L. White, et al., "Attaining Low Moisture Levels in Hermetic Packages," *IEEE/Proc. IRPS*, 1982, pp. 253-259. (1).

David P. Galloway and My N. Nguyen, "A New, Reliable Snap Cure Die Attach Adhesive," *Mat. Res. Soc. Symp. Proc.*, vol. 264, 1992, pp. 271-280.

Sue Oliver, et al., "Silver/Polymer Die Attach for Ceramic Package Assembly," 1992 IEPS meeting, Sep. 27-30, 1992.

My N. Nguyen and Michael B. Grosse, "Low Moisture Polymer Adhesive for Hermetic Packages," *IEEE Trans. on Components, Hybrids and Manufacturing Technology*, vol. 15, No. 6, Dec. 1992, pp. 964-971.

Richard H. Estes, "A Practical Approach to Die Attach Adhesive Selection," *Hybrid Circuit Technology*, Jun. 1991.

Tom Ramsey and Gail Heinen, "Controlling Moisture in Ceramic Packages," *Semiconductor International*, Aug. 1988.

Mitsubishi Gas Chemical Company, Inc., "High Heat Resistant BT Resin—Bismaleimide-Triazine Resin," Fourth Edition, Sep. 1, 1984.

Sue Oliver, "Qualification Status and Extended Stressing of JM7000 Silver/Polymer Die Attach Adhesive for Ceramic Package Assembly," Jan. 12, 1993.

Hi-Tek Polymers, "AroCy® F-10 Cyanate Ester Monomer," Apr. 1989.

Hi-Tek Polymers, "AroCy® B-30 Cyanate Ester Semisolid Resin," Oct. 1988.

Andrew Rosenbaum, "Smarter and Smarter," Electronics, Oct. 1991, 32D & 32E (2).

Daniel Webb, "What Future is in the PC Cards?" Electronic Business, Nov. 4, 1991, p. 11 (2).

"Japan Challenges Intel's Lead in Flash Memories," attached chart World EPROM Market, Semiconductors (2).

LOW TEMPERATURE FLEXIBLE DIE ATTACH ADHESIVE AND ARTICLES USING SAME

CROSS-REFERENCE TO RELATED APPLICATION

This is a continuation of application Ser. No. 07/843,738 filed Feb. 28, 1992, now abandoned and a continuation-in-part of application Ser. No. 07/602,504 filed Oct. 24, 1990, now U.S. Pat. No. 5,150,195, dated Sep. 22, 1992.

FIELD OF THE INVENTION

The present invention relates to a flexible die attach adhesive. The flexible die adhesive can be modified to be capable of developing very good adhesive strength at low curing temperatures. One embodiment of the invention relates to a flexible card for processing in a computer that includes a semiconductor device enveloped therein adhered to a substrate by the aforementioned adhesive.

BACKGROUND OF THE INVENTION

As uses for semiconductor devices continue to increase, there is a growing demand for adhesive compositions and formulations capable of securing semiconductor devices to substrates under a variety of conditions. The wide variety of applications using semiconductor devices sometimes require that such adhesive formulations be flexible where the device must be flexible and sometimes that the adhesive formulation be capable of developing very good adhesive strength at low curing temperatures so that significant stress is not imparted to the die and the curing conditions do not adversely affect other components.

One application employing semiconductor devices which is gaining increasing importance is in the field of cards to be processed in computers where such cards incorporate one or more semiconductor devices and are therefore able to store more information than magnetic cards. Such cards may be useful over a broad spectrum of applications including, for example, credit and telephone cards. These cards, which are referred to as "smart cards" must be thin and must be able to bend without breaking, i.e., the card and card components must be flexible.

Typically, "smart cards" are constructed of a material such as polyester reinforced with glass fibers and have enveloped within the card one or more semiconductor devices. Desirably, such devices should be secured within the card by a die attach adhesive which is flexible but which provides very good adhesive strength and does not impart stress to the die during curing. It is also important that the adhesive be capable of being cured at relatively low temperatures to facilitate fabrication of the cards without damage to the card or the semiconductor devices.

Cards including semiconductor devices enveloped therein are disclosed in an article by Hans Steinegger, Microelectronics Manufacturing Technology, pp. 13-15, Dec. 1991; the disclosure of which is expressly incorporated herein by reference. As disclosed in the aforementioned article, the semiconductor devices have heretofore been bonded directly to a metal conductor or other substrate using an epoxy adhesive followed by encapsulation with epoxy resin. The obstacles to the production of such "smart cards" include problems arising in wire bonding because the basic material of the film is not as heat resistant as might be desired. It is pointed out in the article that wire bonding must be performed at temperatures that do not exceed 180° C. It is apparent therefor that there is a need for a flexible die attach adhesive which is capable of being cured at relatively low temperatures but has very good adhesive strength.

SUMMARY OF THE INVENTION

In a copending application I described adhesive formulations which are rapidly curing, i.e., are capable of being cured in under 5 minutes at 200° C. However, these formulations contain cyanate esters and are not flexible. The present invention provides a method of rendering cyanate esters flexible by reacting therewith at least one elastomeric and thermoplastic modifier from the group of hydroxyl (—OH), amine (NH) or epoxide reactive groups, or mixtures thereof by, for example, grafting such groups to cyanate molecular structures.

In addition to the foregoing, the invention includes adhesive formulation for bonding a semiconductor device to a substrate, which comprises a reaction product of cyanate ester and the elastomeric modifier, as discussed above, having a low glass transition temperature of less than about 25° C. To impart rapid curability at low temperature, the adhesive may include an alkylphenol, a metal-containing curing catalyst, and/or silver in the form of flakes or powder. Advantageously, the alkylphenol is nonylphenol, the metal-containing curing catalyst is from the group consisting of cobalt acetylacetonate and copper napthenate and the silver is present in amounts up to 90 wt. %. In a preferred embodiment the adhesive comprises the reaction product of 6 to 24 wt. % modifier and 4 to 16 wt. % cyanate ester, 0.01 to 0.06 wt. % metal-containing curing catalyst, 0.5 to 2 wt. % alkylphenol and up to 90 wt. % silver flake and/or powder. Where alkylphenol and/or metal containing catalyst are present as little as 4 to 20% silver may be sufficient. Where these curing catalysts are absent 60 to 90 wt. % silver may be needed to impart rapid curability to the adhesive formulation.

A novel card in accordance with the invention, for processing in a computer, comprises a semiconductor device enveloped within the card and adhered with a flexible adhesive to a substrate. The substrate is advantageously a flexible organic polymeric substrate and/or a lead frame or metal conductor. The adhesive comprises the reaction product of cyanate ester and modifier, as described above, having a glass transition temperature of less than about 25° C., and which may include an alkylphenol, a metal-containing curing catalyst and/or silver in the form of flakes and/or powder.

DETAILED DESCRIPTION OF THE INVENTION

As has been previously explained, a flexible adhesive is needed for a number of applications where semiconductor devices with large surface areas are attached to flexible substrates, particularly where there is a significant difference between the thermal expansion coefficients of the silicon of the semiconductor device and the substrates. In such cases, a low-stress die attach adhesive is required for maximum performance. This is especially important where the semiconductor device is to be attached to lead frames, such as copper lead frames, and polymeric substrates such as polyester, polyamide films, etc.

If a conventional rigid adhesive such as epoxy referred to in the aforementioned Steinegger article is used in the above described applications, the thermally induced tensile stress imparted to the surface of the semiconductor die is so high that it usually results in a silicon fracture.

Figure 1:
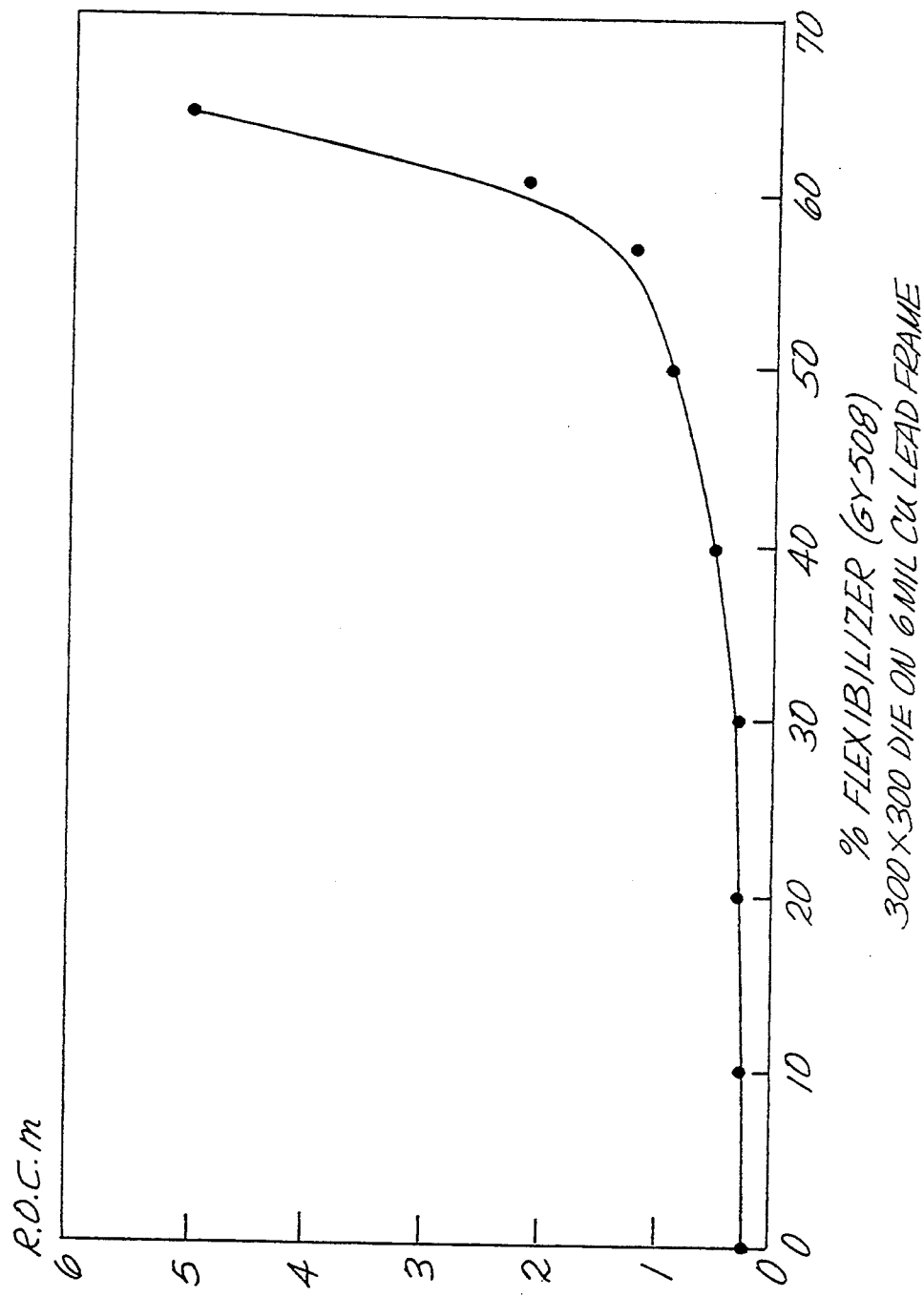
FIG. 1 is a graph showing the relationship between the percentage of modifier, i.e., flexibilizer and radius of curvature ("ROC")

To assess the phenomenon involved it is necessary to measure the die stress. One such method is by determining the radius of curvature ("ROC"). A stress free die would be flat and would have a very large radius of curvature. The relationship between tensile stress imparted on the die surface and the radius of curvature is illustrated in FIG. 1. Since the tensile stress of silicon is about 100 MPa, an ROC value of about 1 meter or above is advantageous to eliminate silicon fracture with dies of customary size.

Die attach adhesive compositions including cyanate ester and silver do not give the flexible properties needed for the above applications. However, flexible properties can be achieved by reacting cyanate esters with at least one elastomeric and thermoplastic modifier from the group of hydroxyl (—OH), amine (NH) or epoxide reactive functional groups, or mixtures thereof by, for example, grafting such group to cyanate ester molecular structures.

To illustrate the foregoing, blends of Tg flexible epoxy and cyanate ester resin undergo the following reactions:

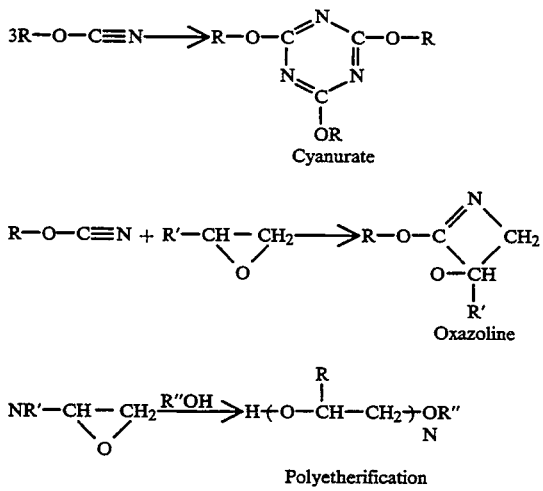

Cyanurate

Oxazoline

Polyetherification

Figure 2:
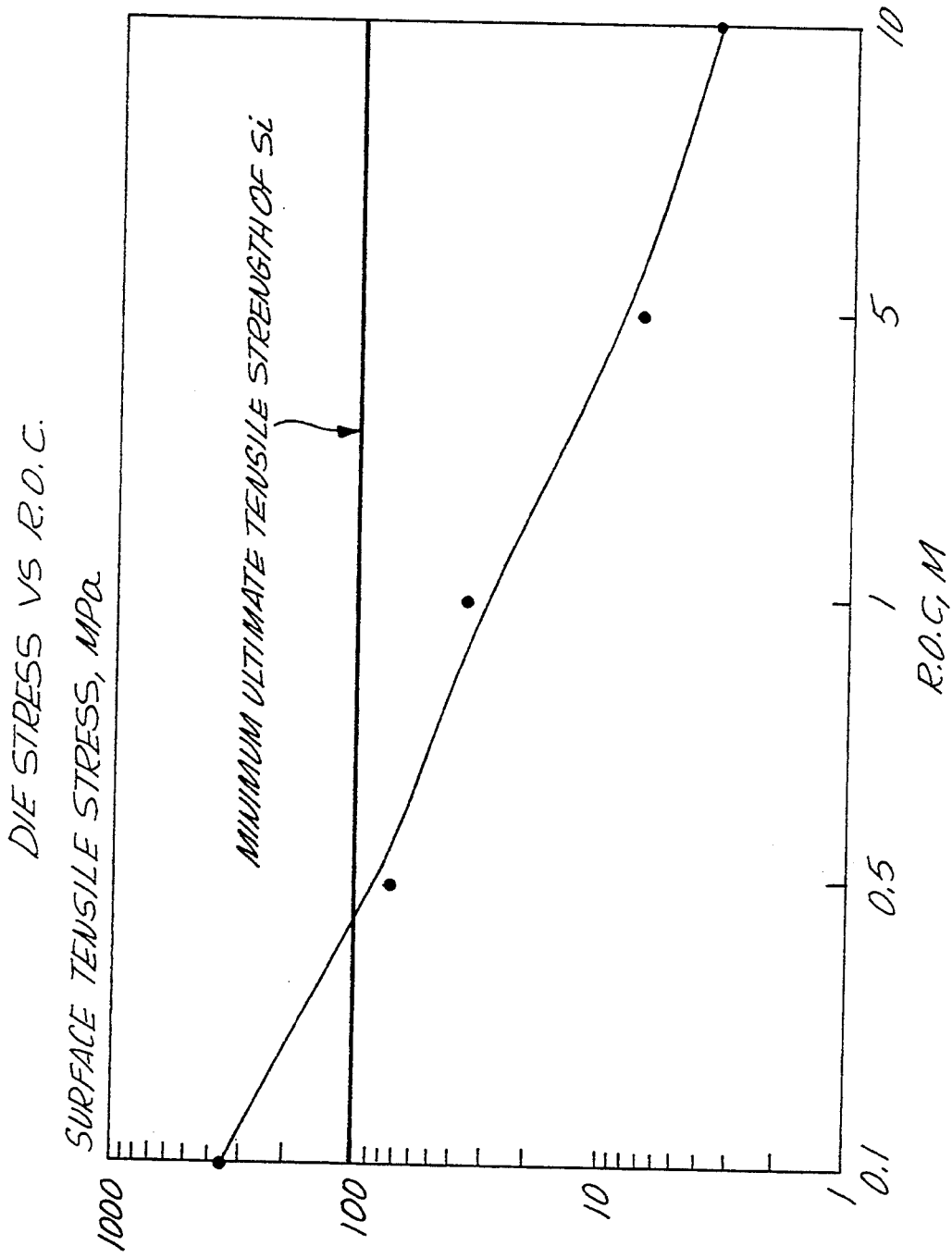
FIG. 2 is a graph of die stress against ROC.

The effect of flexible epoxy on ROC is shown in FIG. 2. As can be seen, a mixture of at least 50% epoxy gives acceptable performance and the cyanate ester in this mixture also acts as a curing agent for the epoxy. However, at least about 15% cyanate ester is needed in the adhesive formulation to provide satisfactory curing in this system. Other elastomeric modifiers containing hydroxyl reactive groups, including hydroxyl terminated butadiene and butadiene-acrylonitrile copolymers, such as "HYCAR" sold by B. F. Goodrich and "VITEL-3600" which is a saturated copolyester resin with a Tg of −11° C., are useful as well as amine functional groups such as polyurethane, elastomer, urethane acrylate, silicone imides, etc.

All of the foregoing modifiers have proven to be miscible with cyanate ester in the uncured state. During curing, the system is phase-separated, forming a co-continuous structure of hard and soft domains composed of cyanate ester-rich and elastomer-rich agglomerates. This system exhibits many advantageous properties, such as increased flexibility due to the soft modifier, while maximizing adhesive strength at high temperature.

The following are examples of the flexible adhesive formulation:

EXAMPLES I–IV

| Composition | I | II | III | IV |
| --- | --- | --- | --- | --- |
| Cyanate Ester L10 | 20 | 20 | 20 | 20 |
| Silicone imide | | | | 20 |
| VITEL 3600 | 20 | | | |
| Urethane acrylate | | | 20 | |
| HYCAR HTBN | | 20 | | |
| Silver flake | 60 | 60 | 60 | 0 |
| Nonylphenol | 1.6 | 1.6 | 1.6 | 1.6 |
| ROC, m | 1.5 | 1.2 | 2.0 | 1.0 |
| Adhesion, | | | | |
| 25 C., kg | 20 | 7.0 | 15 | 20 |
| 300 C. | 1.5 | 0.5 | 1.5 | 1.5 |

EXAMPLE V

| Composition | V |
| --- | --- |
| Epoxy XB4122 | 14.57 |
| Arocy L10 | 9.71 |
| Cu Napthenate | 0.018 |
| Nonylphenol | 0.702 |
| Ag flake | 75.0 |
| Total | 100.0 |

| Curing Schedule | Die Shear, kg |
| --- | --- |
| - cure 5 min, 125 C. | 5.6 |
| - cure 1 hr, 125 C. | 10.0 |

Figure 3:
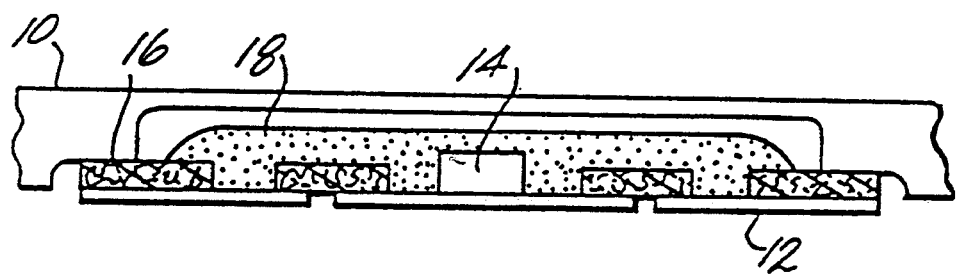
FIG. 3 is a schematic view partly in section of a card within which one or more semiconductor devices are enveloped and showing such devices bonded to a substrate.

A so-called "smart card" is shown in the schematic illustration depicted in FIG. 3. As can be seen, a card 10, usually made of plastic, includes a metal conductor 12 to which is bonded a semiconductor device 14. Glass fiber reinforced polyester pads 16 may be included and the entire device is encapsulated, such as within an epoxy resin 18. The epoxy resin may be ground flat to produce a thin plastic card.

The adhesive formulation of the present invention is especially suitable for bonding the semiconductor device to a substrate because it is capable of being cured at comparatively low temperatures of 100° to 130° C. and has very good adhesive strength while imparting low stress on the die. It is highly desirable for smart card application to employ a die attach adhesive capable of being cured at temperatures not substantially greater than about 130° C. The die may be attached to a lead frame, such as a copper lead frame, in which case the low temperature curing adhesive minimizes oxidation of the copper and thereby eliminates the need of nitrogen or other inert atmosphere such as is often used in curing ovens.

The following examples are of flexible adhesive compositions used to bond semiconductor devices suitable for smart card manufacture.

TABLE I

| Flexible adhesive composition: | |
| --- | --- |
| Arocy L10 | 9.71% |
| XB4122 | 14.57% |
| Copper Napthenate, 8% Cu | 0.02% |
| Nonylphenol | 0.70% |
| Ag Flakes | 75.00 |

The cyanate ester Arocy L10 is available from Rhone-Poulenc of Louisville, Ky. The modified bisphenol epoxy resin such as XB 4122 or XUGY 376 is a flexible epoxy supplied by Ciba Geigy. The catalyst system is a solution of copper napthenate or copper acetylacetonate in nonylphenol. The silver flake has the same physical properties described in the previous examples. Adhesive strength results appear in the following table.

TABLE II

| ADHESION - LAP SHEAR | | |
| --- | --- | --- |
| Die Backside 5 MIN CURE | Bore Si Die | Gold Coated Si Dies |
| X avg. | 5.7 Kg | 6.6 Kg |
| Standard Deviation | 2.1 Kg | 3.9 Kg |
| Min Value | 3.2 Kg | 2.5 Kg |
| Max Value | 9.3 Kg | 14.9 Kg |

Substrate: Polyester film - Cu lead frame - Ni plated - Au flash
Curing temperature: 125 ± 5° C.
Die size: 5.5 × 4.5 mm - 217 × 177 mils.

The following is another example of a low curing adhesive formulation:

TABLE III

| Arocy L10 | 25% |
| --- | --- |
| Copper Napthenate, 8% | 0.04% |
| Nonylphenol | 1% |
| Ag flakes | 75% |

The catalysts in the foregoing system may be copper napthenate or copper acetylacetonate, nonylphenol and silver. The formulation in Example III was cured at 100° C. for 15 minutes and exhibited an adhesive strength of over 30 Kg for a semiconductor die X150 attached on a copper lead frame.

It is apparent from the foregoing that various changes and modifications may be made without departing from the spirit of the invention. Accordingly, the scope of the invention should be limited only by the appended claims wherein what is claimed is:

1. A flexible adhesive formulation having a ROC value of about 1 meter or above comprising the reaction product of a cyanate ester-containing material and at least one flexibilizer miscible with cyanate ester in the uncured state selected from the group consisting of elastomeric and thermoplastic modifiers selected from the group consisting of hydroxyl, amine, and epoxide reactive functional group containing compounds and mixtures thereof, said cyanate ester comprising a least 15 wt. % of the mixture to be reacted and said flexibilizer having a glass transition temperature less than about 25° C.

2. A flexible adhesive formulation according to claim 1 further comprising silver in an amount sufficient to function as a curing catalyst and to render said adhesive curable in not greater than 5 minutes at 200° C.

3. A flexible adhesive formulation according to claim 1 further comprising an alkylphenol, a metal-containing curing catalyst and an electrically and/or thermally conductive filler.

4. A flexible adhesive formulation according to claim 3 wherein said filler comprises silver in an amount of 60 to 90 wt. % of the formulation.

5. A flexible adhesive formulation according to claim 3 comprising 0.01 to 0.06 wt. % metal curing catalyst, 0.5 to 2 wt. % alkylphenol and up to 90 wt. % silver.

6. A flexible adhesive formulation according to claim 5 comprising 4 to 20 wt. % silver.

7. A flexible adhesive formulation according to claim 1 further comprising an electrically and/or thermally conductive filler.

8. A flexible adhesive formulation according to claim 7 comprising 60 to 90 wt. % silver.

9. A flexible adhesive formulation according to claim 1 further comprising up to 90 wt. % silver.

* * * * *